（12）United States Patent
Sauer

(10) Patent No.: US 11,103,126 B2
(45) Date of Patent: Aug. 31, 2021

(54) SURGICAL EQUIPMENT HOLDER

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 16/610,311

(22) PCT Filed: May 3, 2018

(86) PCT No.: PCT/US2018/030846
§ 371 (c)(1),
(2) Date: Nov. 1, 2019

(87) PCT Pub. No.: WO2018/204612
PCT Pub. Date: Nov. 8, 2018

(65) Prior Publication Data
US 2020/0077872 A1    Mar. 12, 2020

Related U.S. Application Data

(60) Provisional application No. 62/500,972, filed on May 3, 2017.

(51) Int. Cl.
*F16M 11/00*    (2006.01)
*A61B 1/00*    (2006.01)
*A61B 90/50*    (2016.01)
*F16M 11/14*    (2006.01)

(52) U.S. Cl.
CPC .......... *A61B 1/00149* (2013.01); *A61B 90/50* (2016.02); *F16M 11/14* (2013.01); *F16M 2200/021* (2013.01); *F16M 2200/066* (2013.01)

(58) Field of Classification Search
None
See application file for complete search history.

(56) References Cited

U.S. PATENT DOCUMENTS

| 3,910,538 A | 10/1975 | Baitella |
| 5,609,565 A | 3/1997 | Nakamura |
| 5,779,209 A | 7/1998 | Rello |

(Continued)

FOREIGN PATENT DOCUMENTS

| JP | 2843507 | 1/1999 |
| WO | 2016160272 | 10/2016 |

OTHER PUBLICATIONS

Jul. 6, 2018 International Search Report; Copenheaver, Blaine R., International Search Report for PCT/US2018030846.

(Continued)

*Primary Examiner* — Steven M Marsh
(74) *Attorney, Agent, or Firm* — Michael E. Coyne; Christopher B. Miller

(57) ABSTRACT

A surgical equipment holder is disclosed. The surgical equipment holder includes a first arm pivotable relative to a base, a second arm pivotably coupled to the first arm and an end effector pivotable relative to the second arm. The surgical equipment holder also includes a lever configured to actuate between a locked and unlocked position by use of a single hand by an operator. The end effector of the surgical equipment holder is configured to support and finely adjust the position of any number of surgical accessories during surgical procedures.

4 Claims, 3 Drawing Sheets

(56) References Cited

U.S. PATENT DOCUMENTS

| | | | | |
|---|---|---|---|---|
| 6,471,165 | B2* | 10/2002 | Twisselmann | F16M 11/18 |
| | | | | 248/123.11 |
| 8,132,769 | B2* | 3/2012 | Metelski | G02B 21/0012 |
| | | | | 248/281.11 |
| 8,424,823 | B2* | 4/2013 | Fadler | F16M 11/24 |
| | | | | 248/288.31 |
| 9,437,469 | B2* | 9/2016 | DiBella | H01L 21/68707 |
| D800,814 | S* | 10/2017 | Matuschek | D16/131 |
| 10,352,497 | B2* | 7/2019 | Yokiel | F16M 11/24 |
| 10,788,160 | B2* | 9/2020 | Elias | F16M 11/2078 |
| 2002/0077531 | A1 | 6/2002 | Puchovsky et al. | |
| 2011/0190592 | A1 | 8/2011 | Kahle et al. | |
| 2019/0328475 | A1* | 10/2019 | Arai | A61B 34/30 |
| 2019/0328479 | A1* | 10/2019 | Wada | B25J 3/00 |

OTHER PUBLICATIONS

Aug. 13, 2018 International Search Report; Young, Lee W., International Search Report for PCT/US2018033288.

European Search Report, dated Dec. 2, 2020, Milles, Julien, Search Report from Related EP18794221 application.

Australian Examination Report, dated Jul. 11, 2020, Violante, Karen, Examination Report from Related AU2018263972 application.

Japan Office Action, dated Apr. 6, 2021, Kogani, Takumi, Foreign Office Action from Related JP2019-558765 application.

\* cited by examiner

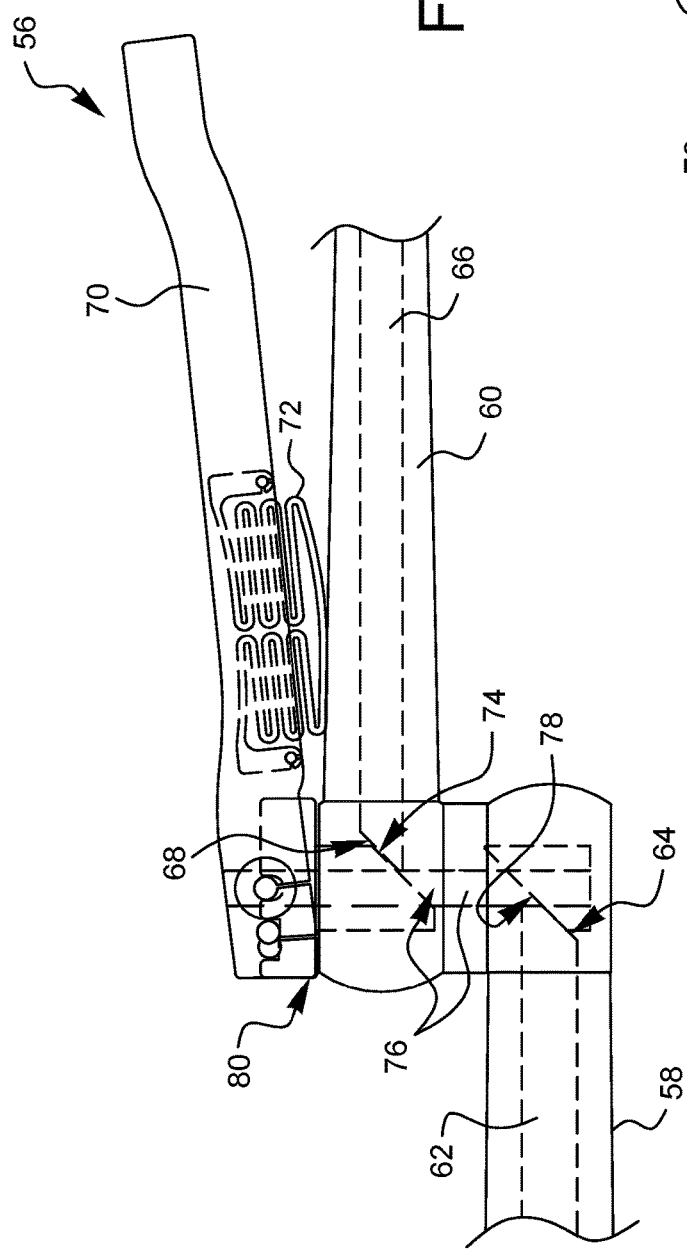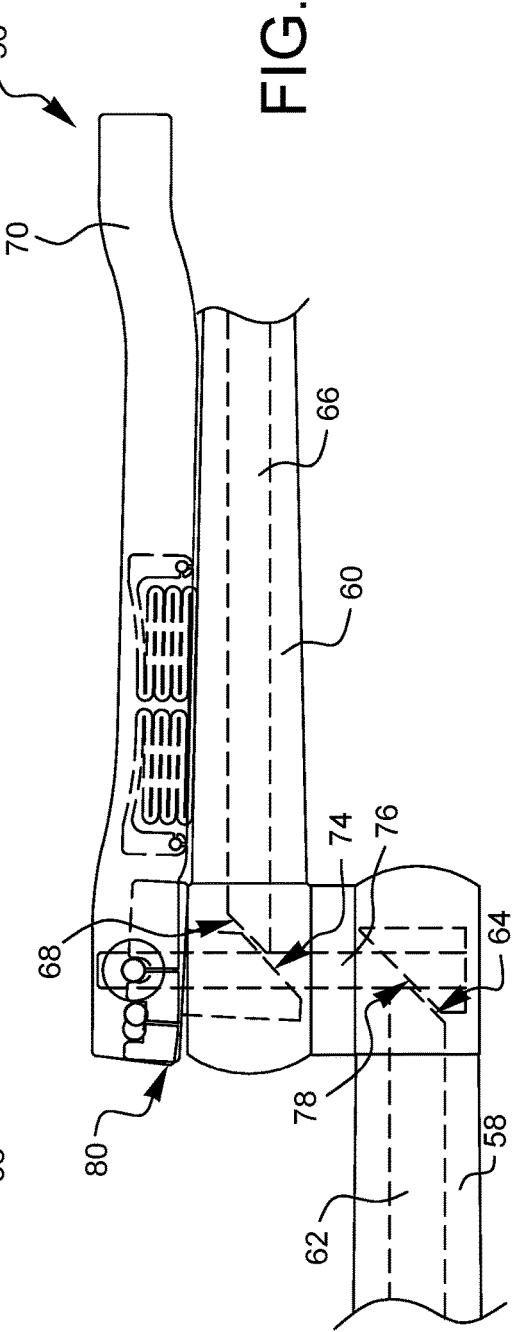

SURGICAL EQUIPMENT HOLDER

RELATED APPLICATIONS

This patent application claims priority to PCT Application PCT/US2018/030846 entitled "SURGICAL EQUIPMENT HOLDER" filed May 3, 2018, which claims priority to U.S. Provisional Patent Application No. 62/500,972 filed May 3, 2017 and entitled, "SURGICAL EQUIPMENT HOLDER". The entire 62/500,972 and PCT/US2018/030846 applications are hereby incorporated by reference in their entirety.

FIELD

The claimed invention relates to surgical devices, and more specifically to an adjustable holder for surgical equipment.

BACKGROUND

Laparoscopic, endoscopic, and other types of minimally invasive surgical procedures often rely on percutaneous introduction of surgical instruments into an internal region of a patient where the surgical procedure is to be performed. Surgeons continue to find it desirable to utilize smaller and smaller access incisions in order to minimize trauma and reduce patient recovery times. Frequently, surgeons will make additional small incisions through which a viewing scope or other surgical equipment may be passed to assist in the operation. In the case of viewing scopes, an assistant may manipulate and/or hold the scope in a fixed position for the surgeon so that the surgeon may look at images, acquired by the scope, on a monitor screen in order to perform the minimally invasive operation. Holders, such as the one illustrated in FIG. 1, may be used in lieu of an assistant to position and hold surgical equipment such as, but not limited to, a viewing scope.

FIG. 1 is a schematic illustration of a prior art equipment holder 20. The equipment holder 20 has a base 22. The base 22 is illustrated schematically, but may be an object with substantial mass compared to what it will be holding so that the equipment holder 20 is stable. Alternately, the base 22 may be a clamp, suction device, magnet, or otherwise have an attachment mechanism for attaching or coupling the equipment holder 20 to a surgical operating table or some other equipment in an operating room. Such bases are known to those skilled in the art.

A ball connector 24 is coupled to the base 22. A first arm 26 is pivotably coupled to the ball connector 24 by a socket 28 on one end of the first arm 26. The socket 28 is sized so that it does not come off the ball connector 24, but otherwise is able to pivot freely in all directions around the ball connector 24. The other end of the first arm 26 terminates in a receiver 30 which has a threaded opening (not visible in FIG. 1) sized to accept a screw (also not visible in FIG. 1) which is attached to control knob 32. The screw 34 attached to control knob 32 can be seen in FIG. 2. FIG. 2 is a partially exploded view of the prior art equipment holder 20 of FIG. 1. When assembled, the screw 34 passes through a clearance hole 36 in the first end 38 of a second arm 40 and is screwed into the threaded opening 42 of receiver 30. A rod 44 is slideable within the first arm 26. The rod 44 may have a cupped end 46 which is designed to help create friction against the ball connector 24 when the rod 44 is pushed towards the ball connector 24. The rod 44 also has a tapered end 48 opposite the cupped end 46. When the screw 34 is not tightened all the way into the threaded opening 42 of the receiver 30, the end of the screw 50 does not exert enough force on the tapered end 48 of the rod 44 to push the rod 44 against the ball connector 24. Furthermore, when the screw 34 is not tightened all the way into the threaded opening 42 of the receiver 30, the second arm 40 is free to rotate around an axis defined by the screw 34. Thus, while the screw 34 is not tightened, a surgeon may use one hand to position the second arm 40 as well as the first arm 26 coupled to it. Then, while using that one hand to maintain the desired position of the arms, the surgeon may use his/her other hand to tighten the control knob 32 to lock the first and second arms of the equipment holder 20 in place. As the control knob 32 is tightened, the end of the screw 50 interferes with the tapered end 48 of the rod 44, pushing the rod 44 axially against the ball connector 24 and fixing the orientation of the first arm 26. Additionally, the tightening of the control knob 32 grips the first end 38 of the second arm 40 between the control knob 32 and the receiver 30, thereby fixing the orientation of the second arm 40 as illustrated in FIG. 1. Unfortunately, this positioning and locking into a desired position takes two hands.

Furthermore, this two-handed adjustment does nothing to adjust an end effector 52 coupled to a second end 54 of the second arm 40. Many prior art equipment holders 20 have an adaptor or end effector 52 configured to provide an interface with the surgical tool being held. In the case of a viewing scope, the end effector 52 would have some type of clamp or set screw, or other attachment features which actually hold the viewing scope. In FIGS. 1 and 2, the end effector 52 is simply shown as a generic block, but some end effectors may also have a separate control knob whereby the angle of the device being held by the end effector 52 can be changed relative to the second arm 40. Such an adjustment, while providing positioning flexibility, would also require a pair of hands to work and could not be done at the same time as the adjust of the first and second arm 26, 40 positions unless two people were involved at the same time. Therefore, it would be desirable to have an improved surgical equipment holder, especially one which was simpler to adjust.

SUMMARY

A surgical equipment holder is disclosed. The surgical equipment holder has a first arm pivotable relative to a base, a second arm pivotably coupled to the first arm, an end effector pivotable relative to the second arm, and a lever movable between a locked position and a released position. The lever is configured such that the first arm does not pivot relative to the base, the second arm does not pivot relative to the first arm, and the end effector does not pivot relative to the second arm when the lever is in the locked position; and the first arm may be pivoted relative to the base, the second arm may be pivoted relative to the first arm, and the end effector may be pivoted relative to the second arm when the lever is in the released position.
arm when in the locked position.

BRIEF DESCRIPTION OF DRAWINGS

FIG. 3A is a side view of a portion of the improved embodiment of a surgical equipment holder in an unlocked position.

FIG. 3B is a side view of a portion of the surgical equipment holder from FIG. 3A in a locked position.

DETAILED DESCRIPTION

Figure 1:
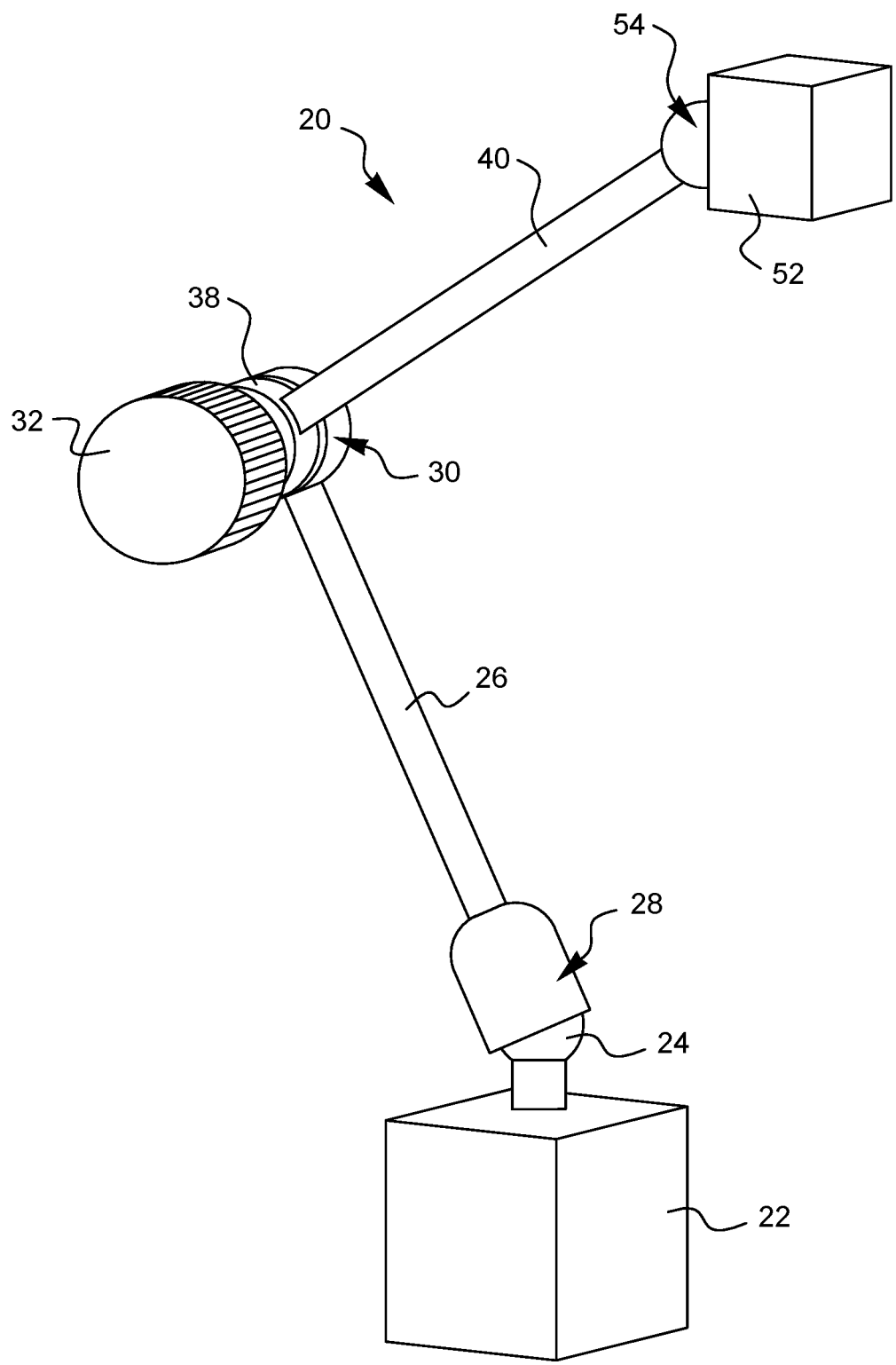
FIG. 1 is a schematic illustration of a prior art equipment holder.
Figure 2:
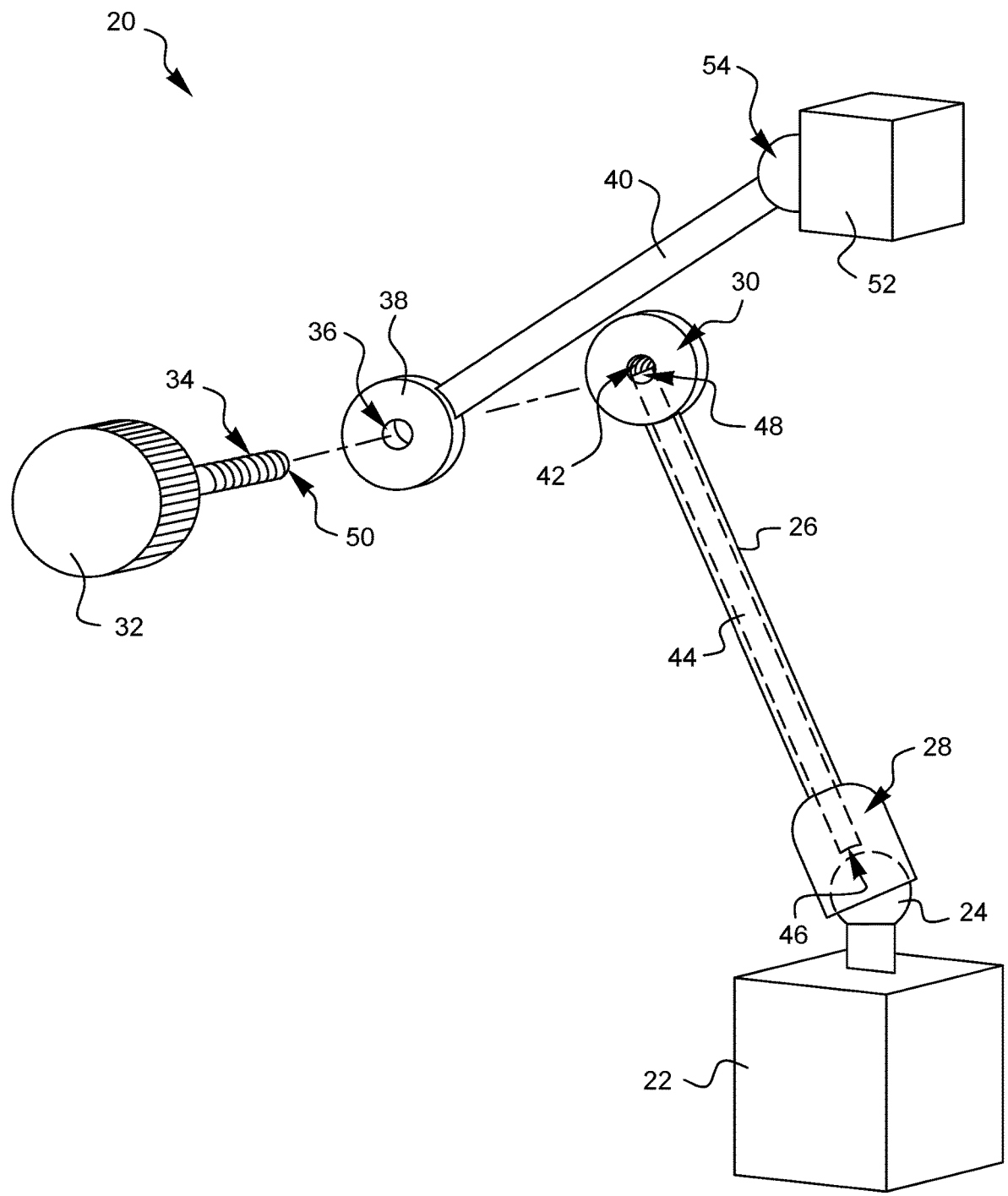
FIG. 2 is a partially exploded perspective view of the prior art equipment holder of FIG. 1.

FIG. 3A illustrates an improved embodiment of a surgical equipment holder 56. Shown is a first arm 58 and a second arm 60. The first arm 58 has a rod 62 slideable therein, the rod 62 having a tapered end 64 on one end. The other end of rod 62 is not visible in this view, but it is configured to interface with a ball connector like the ball connector 24 of the device in FIG. 1. This ball connector could be coupled to a base. The second arm 60 has a rod 66 slideable therein, the rod 66 having a tapered end 68 on one end. The other end of rod 66 is not visible in this view, but it is configured to interface with another ball connector. This ball connector could be coupled to an end effector. A lever 70 is aligned with one of the arms, in this embodiment, with the second arm 60, with the majority of the lever 70 biased away from the arm 60 by a spring element 72. Although a specific style of spring is shown in the example of FIG. 3A for the spring element 72, it should be understood that those skilled in the art are familiar with a wide variety of springs that could be used in place of the illustrated spring element 72.

The lever 70 is coupled to a wedge 74. When the lever 70 is in the position shown in FIG. 3A, the wedge 74 is pressed against tapered end 68 of rod 66 in the second arm 60. This will hold the ball connector (not shown) at the other end of the second arm 60 in position. When the lever 70 is squeezed into the position shown in FIG. 3B, the wedge 74 is pulled away from tapered end 68 of rod 66 in the second arm 60. This will allow the ball connector (not shown) at the other end of the second arm 60 to be moved relative to the second arm 60.

Lever 70 is also coupled to a post 76 which passes through an opening in wedge 74. A wedge 78 is coupled to the post 76. When the lever 70 is in the position shown in FIG. 3A (a locked position), the wedge 78 is pulled up against tapered end 64 of rod 62 in the first arm 58. This will hold the ball connector (not shown) at the other end of the first arm 58 in position. When the lever 70 is squeezed into the position shown in FIG. 3B (a released position), the post 76 is pushed down with the lever, causing the wedge 78 to push away from the tapered end 64 of rod 62 in the first arm 58. This will allow the ball connector (not shown) at the other end of the first arm 58 to be moved relative to the base (also not shown).

Furthermore, when lever 70 is in the position shown in FIG. 3A, a clamping end 80 of the lever 70 is pressed against the end of the second arm 60 while the post 76 and wedge 78 also help to create a clamping force which holds the position of the first arm 58 relative to the second arm 60. When the lever is squeezed into the position shown in FIG. 3B, the clamping end 80 of the lever 70 is lifted from the second arm while the post 76 and wedge 78 release a clamping force, thereby allowing the first and second arms 58, 60 to be moved relative to each other. As a result, it can be seen that this one control feature, lever 70, may be squeezed with a single hand to simultaneously defeat three different locking points. This allows the surgeon to hold the lever with one hand (squeezing the lever) while the other hand positions the scope held by the end effector. During positioning, all degrees of freedom are available to the surgeon and the scope should be very easy to position. Once the desired scope position is established, the surgeon simply releases the lever 70 and all three locking points are again locked into position (for example: 1) the position of the first arm relative to its ball connector, 2) the position of the first arm relative to the second arm, and 3) the position of the second arm relative to its ball connector.) In the prior art devices, this would have taken at least two people and four hands to accomplish, so this embodiment offers clear advantages over the prior art.

Various advantages of a surgical equipment holder have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical equipment holder, comprising:
   a first arm pivotable relative to a base;
   a second arm pivotably coupled to the first arm, wherein the first arm and the second arm are configured to pivot about a substantially inflexible post;
   an end effector pivotable relative to the second arm; and
   a lever movable between a locked position and an unlocked position and configured such that:
   a) the first arm does not pivot relative to the base, the second arm does not pivot relative to the first arm, and the end effector does not pivot relative to the second arm when the lever is in the locked position; and
   b) the first arm may be pivoted relative to the base, the second arm may be pivoted relative to the first arm, and the end effector may be pivoted relative to the second arm when the lever is in the unlocked position.

2. The surgical equipment holder of claim 1 further comprising a spring coupled to the lever.

3. The surgical equipment holder of claim 2 wherein the lever is configured to be in the unlocked position when the lever is squeezed towards the second arm.

4. The surgical equipment holder of claim 2 wherein the lever is configured to be in the locked position when the lever is not squeezed.

* * * * *